(12) United States Patent
Miksza et al.

(10) Patent No.: US 9,788,827 B2
(45) Date of Patent: Oct. 17, 2017

(54) METHOD AND MEANS TO ATTACH ANCHOR SUTURE ONTO MESH IMPLANTS

(71) Applicant: Ethicon, Inc., Somerville, NJ (US)

(72) Inventors: Anthony Miksza, Nazareth, PA (US); Simon Cohn, Lebanon, NJ (US)

(73) Assignee: Ethicon, Inc., Somerville, NJ (US)

( * ) Notice: Subject to any disclaimer, the term of this patent is extended or adjusted under 35 U.S.C. 154(b) by 514 days.

(21) Appl. No.: 14/495,251

(22) Filed: Sep. 24, 2014

(65) Prior Publication Data
US 2016/0081686 A1   Mar. 24, 2016

(51) Int. Cl.
| A61B 17/04 | (2006.01) |
| A61B 17/06 | (2006.01) |
| A61F 2/00 | (2006.01) |
| A61B 17/122 | (2006.01) |
| A61B 17/064 | (2006.01) |

(52) U.S. Cl.
CPC ........ *A61B 17/0401* (2013.01); *A61B 17/122* (2013.01); *A61F 2/0063* (2013.01); *A61B 17/0643* (2013.01); *A61B 2017/0409* (2013.01); *A61B 2017/0414* (2013.01); *A61B 2017/0416* (2013.01); *A61F 2220/0016* (2013.01); *A61F 2230/0008* (2013.01); *A61F 2250/0097* (2013.01)

(58) Field of Classification Search
CPC .............. A61B 17/0401; A61B 17/122; A61B 17/0643; A61B 2017/0409; A61B 2017/0416; A61B 2017/0414; A61F 2/0063; A61F 2250/0097; A61F 2220/0016; A61F 2230/0008

USPC .......................................................... 606/230
See application file for complete search history.

(56) References Cited

U.S. PATENT DOCUMENTS

| 3,636,956 A * | 1/1972 | Schneider ........ A61B 17/06166 528/354 |
| 5,171,251 A | 12/1992 | Bregen et al. |
| 5,474,572 A | 12/1995 | Hayhurst |
| 5,964,697 A | 10/1999 | Fowler |
| 5,972,022 A | 10/1999 | Huxel |
| 6,454,777 B1 | 9/2002 | Green |
| 6,582,443 B2 * | 6/2003 | Cabak ................ A61B 17/0469 606/148 |
| 6,610,006 B1 | 8/2003 | Amid et al. |
| 7,435,251 B2 | 10/2008 | Green |
| 7,975,698 B2 | 7/2011 | Browning |
| 8,118,835 B2 | 2/2012 | Weisel et al. |
| 9,039,596 B2 * | 5/2015 | Sater .................. A61B 17/0401 600/29 |
| 2005/0101834 A1 | 5/2005 | Merade |
| 2010/0069930 A1 | 3/2010 | Roslin et al. |
| 2010/0292718 A1 | 11/2010 | Sholev et al. |
| 2011/0082478 A1 | 4/2011 | Glick et al. |
| 2011/0130774 A1 | 6/2011 | Criscuolo et al. |
| 2012/0078300 A1 | 3/2012 | Mayer et al. |

(Continued)

*Primary Examiner* — Julian W Woo
(74) *Attorney, Agent, or Firm* — E. Richard Skula (57) ABSTRACT

Novel stay suture devices and stay suture combinations with meshes are disclosed. The stay suture devices have a clip and a suture. The clip has leg members that are mounted to a hernia mesh implant such that the leg members are locked in a closed configuration. Also disclosed are novel methods of mounting stay sutures to a surgical mesh implant and repairing a body wall defect such as a hernia defect.

20 Claims, 11 Drawing Sheets

(56) References Cited

U.S. PATENT DOCUMENTS

2013/0046133 A1 2/2013 Buie et al.
2013/0110164 A1 5/2013 Milazzo et al.

* cited by examiner

METHOD AND MEANS TO ATTACH ANCHOR SUTURE ONTO MESH IMPLANTS

FIELD OF THE INVENTION

The field of art to which this invention relates is medical devices, more particularly surgical suture attachment devices useful with surgical mesh implants.

BACKGROUND OF THE INVENTION

The repair of body wall defects and hernia defects is well known in the surgical arts. In a body wall defect, in particular a hernia defect, a defect or opening in the body wall allows the inner peritoneum to protrude through the defect forming a hernia sack. Typically, a section of the patient's viscera will protrude through the body wall and is contained within the hernia sack. Although a patient may live with such a body wall defect without any medical intervention, it is known that complications associated with such a condition may arise. First of all, from an aesthetic perspective the bulge associated with the hernia may be relatively unsightly. Secondly, since a section of viscera may protrude through the defect, there is a possibility of strangulation of the protruding section of viscera caused by the musculature surrounding the defect resulting in potential necrosis of the visceral section, typically a section of intestine. In addition, if untreated the hernia defect may grow in size over time, restricting the patient's activities. And, the patient may experience pain and other physical symptoms.

In order to repair a hernia defect, or other body wall defect, a surgical procedure is necessary. The procedure may be open (direct visualization) or closed (indirect visualization), i.e., endoscopic. Although a hernia defect can be surgically repaired by suturing the tissue surrounding the defect together, i.e., approximating the tissue, it is generally accepted that this type of repair may result in long term recurrence of the hernia. The prevailing standard of care for many hernia repair procedures is to implant a surgical mesh over the body wall defect. During the healing process post-implantation, tissue infiltrates into the mesh and the mesh is essentially incorporated into the body wall and serves as a reinforcing structure. In ventral hernia procedures, the mesh implant may be affixed directly to the peritoneum or may be affixed to fascial tissue above the peritoneum. The hernia mesh implants are typically mounted using specially designed surgical tacks and tacking instruments. In addition to using tacks, many surgeons have a preference for additionally mounting stay sutures to a mesh implant. The stay sutures are used to locate the mesh over the body wall defect prior to securing the mesh implant in place with tacks. The stay sutures serve a dual function of initially aiding in the proper positioning of the mesh implant and providing a second level of tissue securement over and above the securement provided by the tacks.

During a typical hernia repair procedure, a suitably sized hernia mesh implant is selected by the surgeon. The implant must be trimmed in the operating room to the appropriate size to effectively provide a support function while minimizing the amount of mesh (i.e., the mass) implanted in the patient. After trimming the mesh implant, the surgeon must then mount the stay sutures to the mesh implant, typically along axes at four opposed sides of the implant (i.e., north-south and east-west). This is a time consuming process requiring the application of multiple surgical knots for each mounted suture, and resulting in knot tower. The surgeon then locates the mesh implant at the appropriate location over the hernia defect using the stay sutures, and each stay suture is pulled through and mounted in the overlying body wall tissue using a standard suture passer/retrieval instrument.

Since conventional hernia mesh implants are provided by the manufacturers in standard sizes and typically rectangular configurations, the mesh implants must be trimmed by the surgeon in the operating room prior to implantation in order to customize and conform the mesh implants to an individual patient's hernia defect and anatomy. This precludes the manufacturer from providing mesh implants with pre-mounted stay sutures. There is a need in this art for novel stay suture devices which are quickly and readily mounted to trimmed hernia mesh implants by the surgeon in the operating room.

SUMMARY OF THE INVENTION

Accordingly, novel stay suture devices are disclosed. The devices have a clip having a first and second opposed leg members connected by a hinge section. The leg members have proximal ends and distal ends, and opposed inner faces. The leg members have a first open configuration and a second closed configuration. There is a locking mechanism associated with the distal ends of the leg members to lock the members in the second closed configuration. A surgical suture is mounted to the clip, preferably slidably mounted. A section of a mesh implant is contained between the inner faces of the leg members.

Another aspect of the present invention is a combination. The combination has a hernia mesh implant and at least one stay suture device. The device has a clip having a first and second opposed leg members connected by a hinge section. The leg members have proximal ends and distal ends, and opposed inner faces. The leg members have a first open configuration and a second closed configuration. There is a locking mechanism associated with the distal ends of the leg members to lock the members in the second closed configuration. A surgical suture is mounted to the clip, preferably slidably mounted. A section of a mesh implant is contained between the inner faces of the jaw members.

Yet another aspect of the present invention is a method of performing a surgical procedure using the above described stay suture devices and stay suture device combinations to repair a body wall defect.

Still yet another aspect of the present invention is a method of mounting a stay suture to a hernia mesh implant using the above described stay suture devices.

These and other aspects and advantages of the present invention will become more apparent from the following description and accompanying drawings.

DETAILED DESCRIPTION OF THE INVENTION

The clips of the novel stay suture devices of the present invention may be made from conventional biocompatible materials. The materials may be absorbable or nonabsorbable. Examples of nonabsorbable materials include metals such as surgical stainless steels, Nitinol, and non-corrosive metals, and ceramics, and the like. The nonabsorbable materials may be nonabsorbable polymeric materials such as polypropylene, polyethylene, polycarbonate, nylon and the like. The absorbable materials will include conventional absorbable polymers such as lactides, glycolides, polydioxanone, epsilon-caprolactone, polylactic acid, polyglycolic acid, and copolymers and blends thereof and equivalents thereof. The surgical sutures useful in the stay suture devices of the present invention include conventional absorbable and nonabsorbable sutures. The sutures may have conventional monofilament or multifilament constructions. Examples of absorbable suture materials include absorbable polyester polymers and copolymers such as lactides, glycolides, polydioxanone, epsilon-caprolactone, polylactic acid, polyglycolic acid, and copolymers and blends thereof and equivalents thereof and the like, and may include conventional materials such as cat gut. Examples of nonabsorbable polymers include polyesters, silk, polyolefins such as polypropylene and polyethylene, nylon, and the like. Commercially available sutures that may be used with the stay suture devices of the present invention include the following sutures manufactured and sold by Ethicon, Inc., Somerville, N.J., 08876, USA such as Coated VICRYL Plus Suture, Coated VICRYL Suture, MONOCRYL Plus Suture, MONOCRYL Suture, PDS Plus Suture, PDS Suture, Surgical Gut Suture—Chromic, Surgical Gut Suture—Plain, PRONOVA Suture, ETHIBOND EXCEL Suture, ETHILON Suture, MERSILENE Suture, NUROLON Suture, PERMAHAND Silk Suture, PROLENE Suture, and the like. The sutures will have a size that is effective to secure the mesh implants in place. Although any size sutures may be used, typically the size of the sutures will range from a size of 2 to 6-0. The hernia mesh implants that can be used in the novel combinations and methods of the present invention can be made from conventional biocompatible materials that may be absorbable, nonabsorbable, or combinations of absorbable and nonabsorbable materials. The nonabsorbable materials include conventional polymers such as polypropylene, polyester, nylon, e-ptfe, and the like. The absorbable polymers include conventional absorbable polymers such as lactides, glycolides, polydioxanone, epsilon-caprolactone, polylactic acid, polyglycolic acid and the like and copolymers and blends thereof and equivalents thereof.

Figure 1:
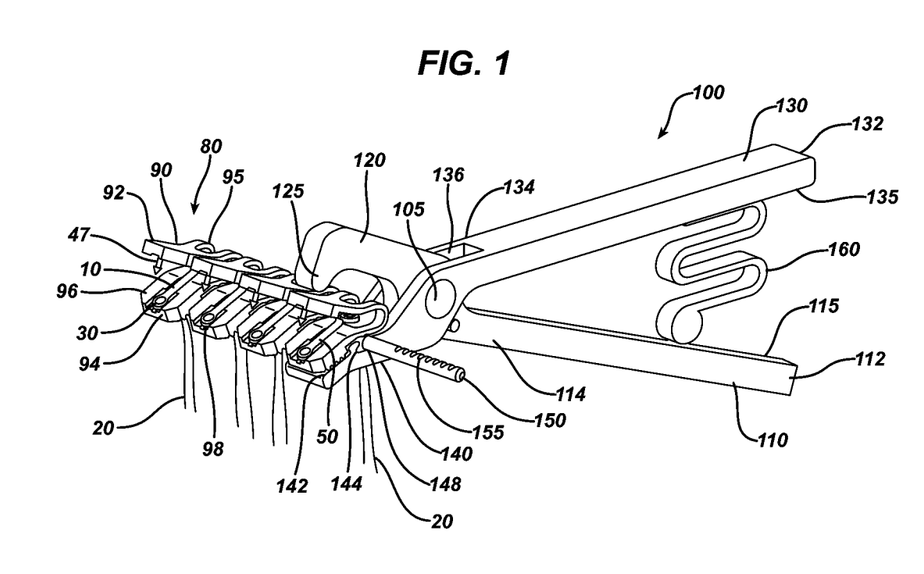
FIG. 1 is a perspective view of multiple novel stay suture devices of the present invention mounted in an applicator.

An applicator instrument 100 loaded with a cartridge 80 containing four (or optionally more) stay suture devices 10 of the present invention is seen in FIG. 1. Applicator 100 is seen to have first and second arm members 110 and 130 hingingly connected together by pin 105. The arm members 110 and 130 are seen to have distal ends 112 and 132, and proximal ends 114 and 134, respectively. Extending distally from distal end 112 of first arm member 110 is the jaw member 120. Jaw member 120 is seen to have downwardly extending engagement member 125. Extending distally from the distal end 134 of arm member 130 is the jaw member 140. The distal end 134 of arm member 130 is seen to have slot 136 for receiving jaw member 120. Jaw member 140 is seen to have inner surface 142 having ridge member 144 for engaging cartridge 80. Extending laterally through jaw member 140 is the passage 148 for slidably receiving the positioning rod 150. The positioning rod 150 is seen to have detents 155 for assisting in gripping the rod 150. Mounted between the inner surfaces 115 and 135 of members 110 and 130 at proximal ends 112 and 132 is the biasing spring member 160. Biasing spring member 160 biases the arm members 110 and 130 such that the jaw members 120 and 140 are biased away from each other in an open position. The biasing spring member 160 is shown to have a sinusoidal configuration, but may have other configurations including leaf springs and helical springs. The cartridge 80 is seen to consist of four cartridge members 90 connected together side by side. Each cartridge member 90 is seen to have upper and lower receiver members 92 and 94, respectively, hingingly connected together at hinge points 95. Extending into the inner surfaces 96 of the receiver members 92 and 94 are cavities 98 for receiving the leg members 40 and 50 of the clips 30 of the stay suture devices 10 of the present invention.

Figure 6:
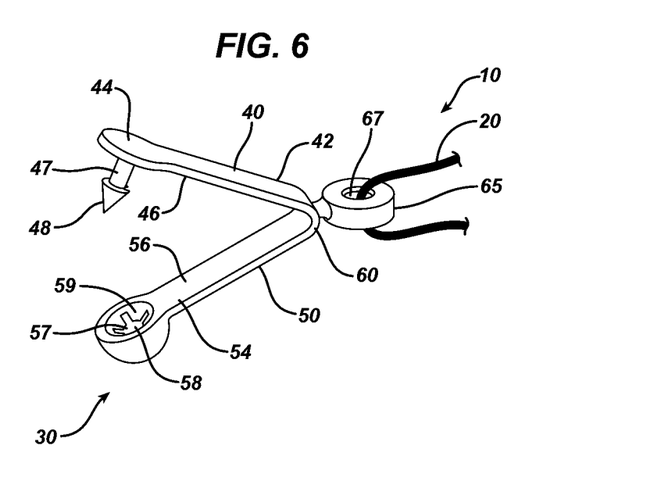
FIG. 6 is a perspective view of an embodiment of a mesh mounting clip useful in the stay suture devices of the present invention; the clip is in the open position with the leg members open and ready to receive a section of mesh between their inner surfaces.
Figure 7:
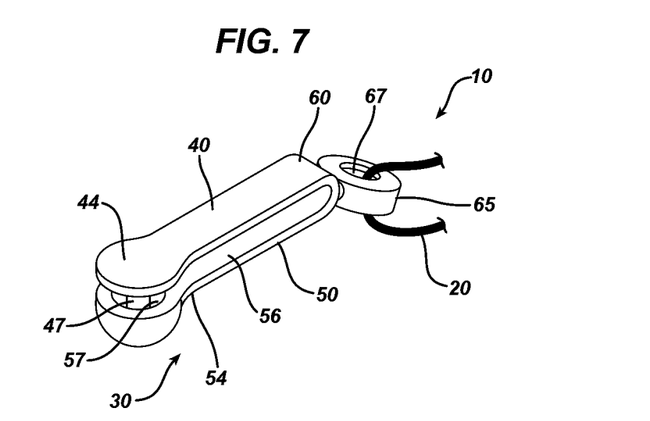
FIG. 7 shows the clip of FIG. 6 in the closed, locked position.

As seen in FIGS. 6 and 7, the suture devices 10 of the present invention are seen to have suture 20 and clip 30. Clip 30 is seen to have first and second opposed leg members 40 and 50 connected by a hinge section 60. The leg members 40 and 50 have proximal ends 42 and 52, distal ends 44 and 54, and opposed inner faces 46 and 56, respectively. Extending down from the inner surface 46 at distal end 44 is the engagement pin 47 having distal piercing barb member 48. Contained in the inner surface 56 of the distal end 54 of leg member 50 is the engagement cavity 57 for receiving and locking the distal barb member 48 of engagement pin 47. Engagement cavity 57 is seen to have a plurality of inwardly extending petal members 59 for engaging barb member 48 about opening 58. The leg members 40 and 50 are seen to have a first open configuration and a second closed, locked configuration. Extending distally from the hinge section 60 is the suture eyelet member 65 having an open passageway 67 for receiving a section of suture strand 20. Suture strand 20 is slidably mounted to eyelet member 65. Although not preferred, suture strand 20 may be fixedly mounted to eyelet member 65.

Figure 2:
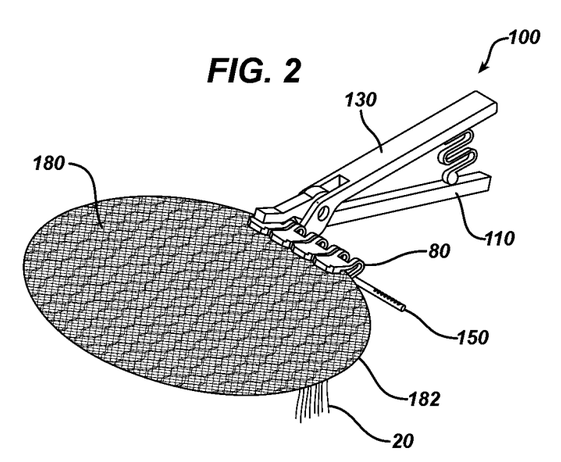
FIG. 2 is a perspective view of the applicator instrument of FIG. 1 positioned at the periphery of a conventional planar hernia mesh implant and shown mounting a first stay suture device to the hernia mesh.
Figure 3:
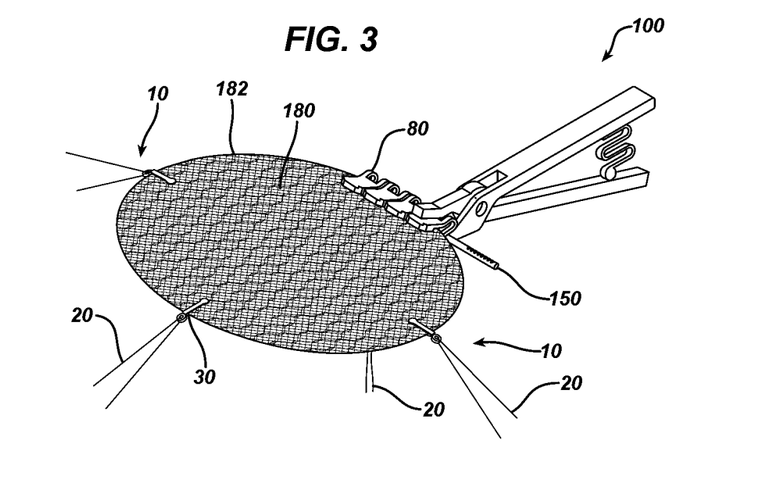
FIG. 3 illustrates the mesh implant of FIG. 2, after three stay suture devices have been mounted; the instrument is in position to mount the last stay suture device.
Figure 4:
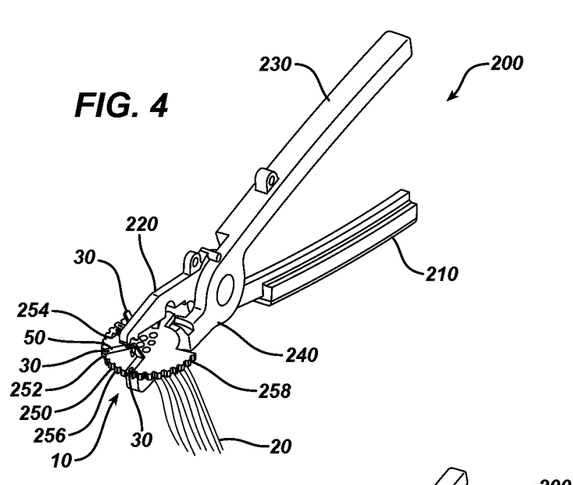
FIG. 4 is a perspective view of an alternate embodiment of an applicator instrument loaded with multiple stay suture devices of the present invention.
Figure 5:
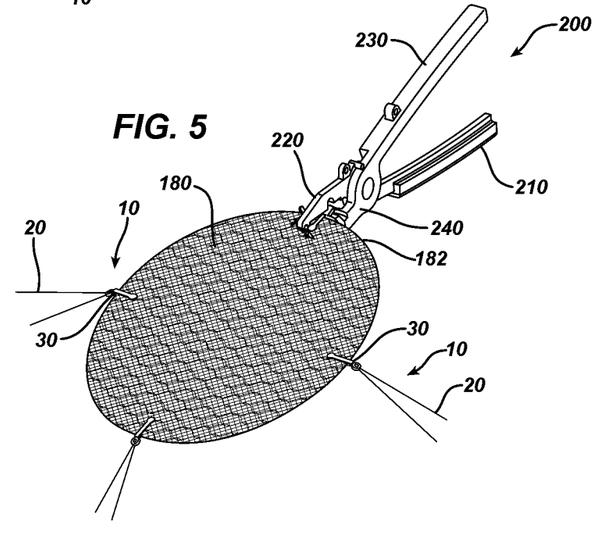
FIG. 5 illustrates the mesh implant of FIG. 4, after three stay suture devices have been mounted; the instrument is in position to mount the last stay suture device.

Referring to FIGS. 2 and 3, an applicator 100 having a cartridge 80 loaded with four stay suture devices 10 of the present invention is seen positioned along the periphery 182 of a trimmed hernia mesh implant 180 adjacent to one axis. The applicator device 100 as shown in FIG. 2 is in position to attach the first stay suture device 10 to the mesh implant 180 from the cartridge 80. FIG. 3 shows the mesh implant 180 after three stay suture devices 10 have been applied. The applicator 100 is in position to attach the last stay suture 10 along the periphery 182 adjacent to the remaining axis. The applicator 100 is used by positioning a section of the periphery 182 of the implant 180 between the leg members 30 and 50 of the clip 20. The applicator 100 is then actuated by squeezing the arm members 110 and 130 together about hinge pin 105, thereby causing the jaw members 120 and 140 to approach each other and move the leg members 40 and 50 toward each other until the engagement pin 47 and distal barb 48 pass through the implant 180 and the pin 47 and barb 48 are locked in cavity 57 by engaging petal members 59. The cartridge 80 is indexed after each device 10 has been applied by engaging the positioning rod 150 and sliding the rod and cartridge until an unfired cartridge member 90 containing a device 10 is indexed between the jaw members 120 and 140. An alternative embodiment of an applicator device 200 is seen in FIGS. 3 and 4. The applicator 200 is similarly seen to have first and second arm members 210 and 230 hingingly connected together by pin 240. The arm members 210 and 230 are seen to have distal jaw members 220 and 240. Mounted to the inner surface of jaw member 240 is rotating cartridge 250. Cartridge 250 is seen to have a semi-circular configuration with cavities 252 extending into top surface 254 of cartridge 240 to receive and retain the second leg members 50 of clips 20. The cartridge 250 is indexed into position by manually rotating the cartridge 250 into position using the radially extending projections 258 extending from periphery 256. As seen in FIG. 5, the applicator 200 is positioned to apply the last stay suture device 10 in the cartridge 250 to the periphery 182 of the mesh implant 180. The applicator 200 is positioned and actuated about the periphery 182 of mesh member 180 in a manner similar to applicator 100 described above, except that the cartridge 250 is rotated to place a device 10 into position for affixation.

Figure 8:
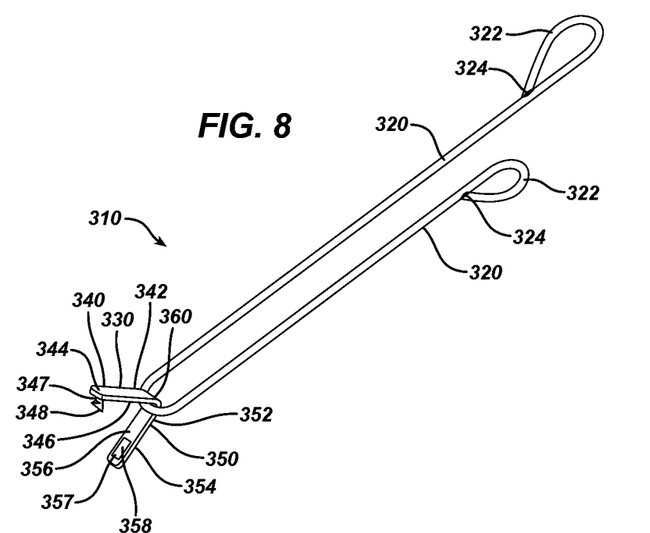
FIG. 8 illustrate an alternate embodiment of a mesh mounting clip useful in the novel stay suture devices of the present invention in an open position; the clip is slidably engaged by a suture having end loops.
Figure 9:
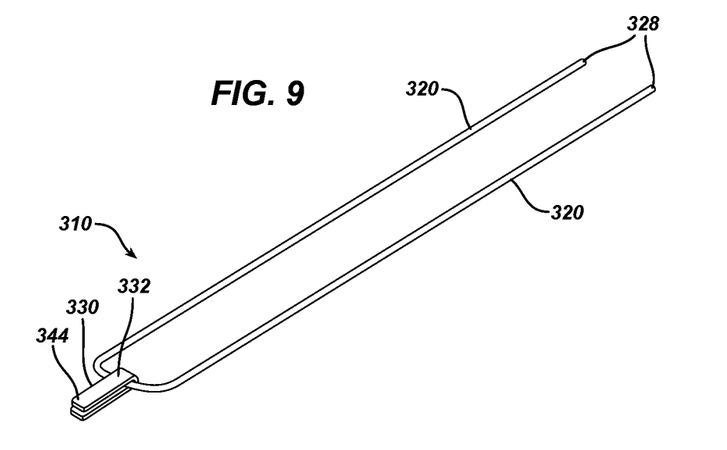
FIG. 9 shows the stay suture device of FIG. 8 with the mesh mounting clip in a closed engagement position; the suture does not have end loops and is slidable between the leg members.

An alternate embodiment 310 of a stay suture device of the present invention is seen in FIGS. 8 and 9. The suture devices 310 of the present invention are seen to have sutures 320 and clips 330. Clip 330 is seen to have substantially flat first and second opposed leg members 340 and 350 connected by a hinge section 360. The leg members 340 and 350 have proximal ends 342 and 352, distal ends 344 and 354, and opposed inner surfaces 346 and 356, respectively. Extending down from the inner surface 346 at distal end 344 is the engagement pin 347 having distal piercing barb member 348. Engagement opening 357 in the inner surface 356 of the distal end 354 of leg member 350 extends therethrough to form engagement cavity 358 for receiving and locking the distal barb member 348 of engagement pin 347. Stay suture 320 is contained between the inner surfaces 346 and 356 of the proximal ends 342 and 352 of the leg members 340 and 350 adjacent to the hinge section 360. The suture 320 is slidable within the locked clip 330. Suture 320 is seen to have optional loops 322 formed by welds 324 in FIG. 8 (although other conventional ways of forming the loops may be utilized) and free ends 328 in FIG. 9. Although not preferred, the suture 320 may be fixedly mounted in clip 330.

Figure 10:
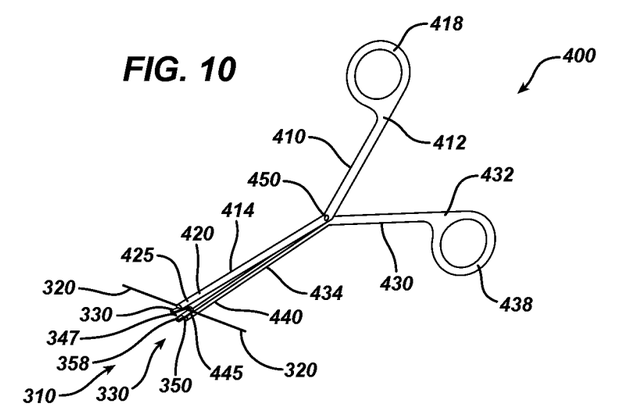
FIG. 10 is a perspective view of a stay suture device of FIG. 9 engaged between the jaws of an applicator instrument; the instrument applies or mounts a single clip at a time to a mesh implant.
Figure 11:
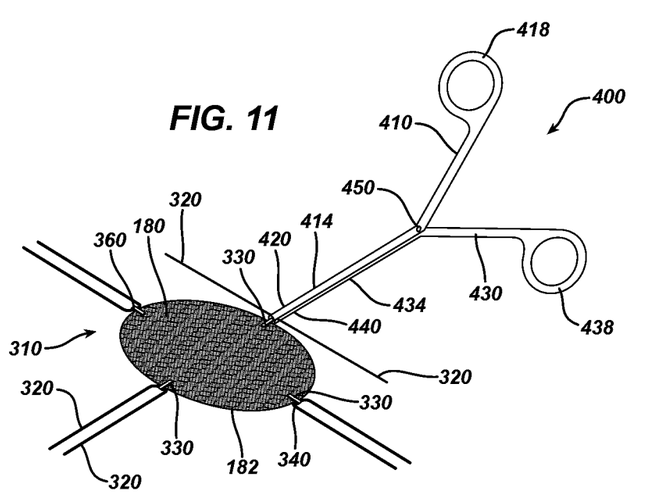
FIG. 11 illustrates the instrument of FIG. 10 showing three stay suture devices mounted about the periphery of a hernia mesh implant; the applicator is positioned to apply the fourth stay suture device.
Figure 12:
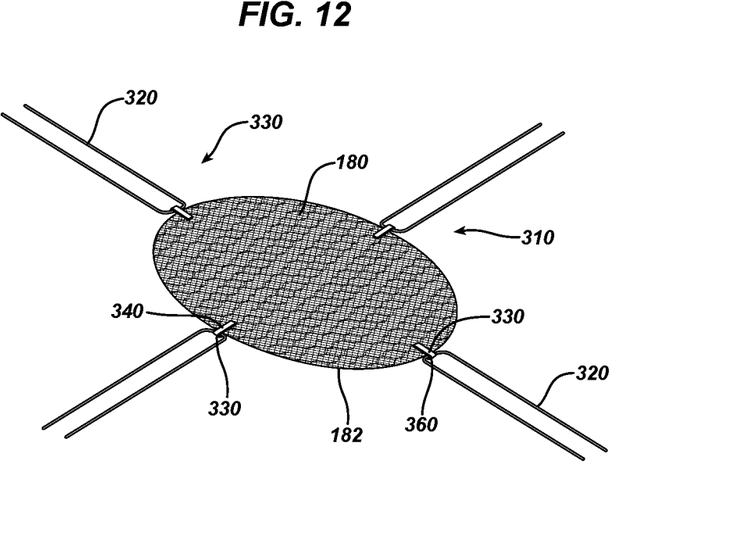
FIG. 12 is a perspective view of the hernia mesh of FIG. 11, showing all four stay suture devices mounted to the mesh; the mesh is now ready for implantation into a patient.
Figure 13:
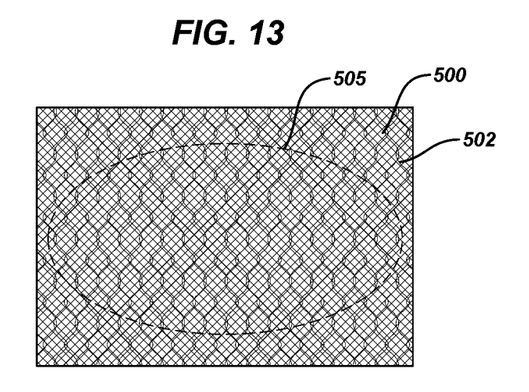
FIG. 13 is a top view of a hernia mesh having a rectangular configuration; an outline of a trim line is shown.
Figure 14:
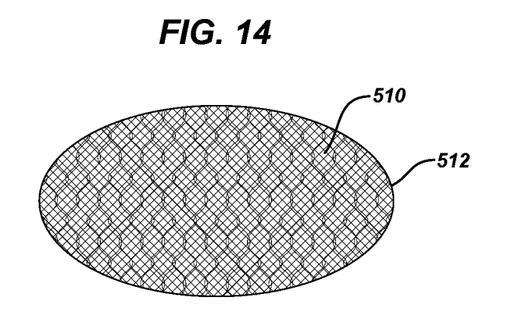
FIG. 14 illustrates the hernia mesh implant of FIG. 13 after the mesh has been trimmed by the surgeon in the operating room to fit over the body wall defect which the mesh will be used to repair.
Figure 15:
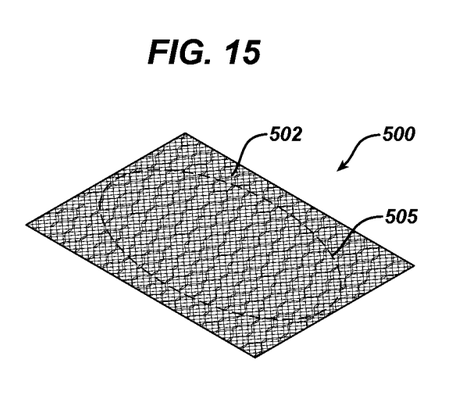
FIG. 15 is a perspective view of the hernia mesh implant of FIG. 13.
Figure 16:
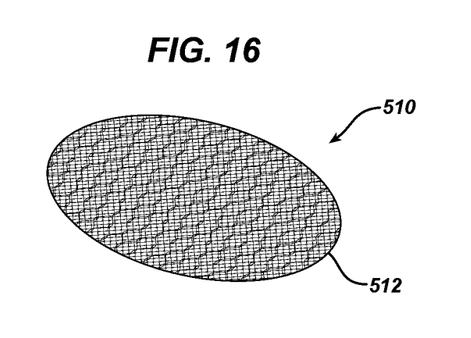
FIG. 16 is a perspective view of the trimmed hernia mesh implant of FIG. 14.

Referring now to FIGS. 10 and 11, an alternate embodiment of an applicator instrument is illustrated. The instrument 400 is seen to have first and second elongated members 410 and 430 hingingly connected by pin 450. Extending from the proximal ends 412 and 432 are the finger rings 418 and 438. Extending from the distal ends 414 and 438 are the jaw members 420 and 440. Jaw members 420 and 440 have upper and lower cavities 425 and 445 for engaging leg members 340 and 350 of clips 330 of stay suture devices 310. As seen in FIG. 11, a stay suture device 310 is mounted to applicator instrument 400 by engaging the leg member 350 in lower cavity 445. The distal end of the clip 330 extends beyond the distal ends of jaw members 420 and 440. Suture 320 is seen to extend from the proximal end of clip 330. As seen in FIG. 11, the device has been used by the surgeon to attached three stay suture devices 310 to the periphery 182 of a trimmed hernia mesh 180 and is shown attaching a final stay suture device 310. The applicator 400 is used to attach the stay suture device 310 by positioning the distal end of the clip 330 in a desired position about the periphery 182 of mesh implant 180 such that a portion of the periphery 182 is contained between the open leg members 340 and 350, and then rotating the finger grips 418 and 438 toward each other about pin 450 to actuate the jaw members 420 and 440 to squeeze the leg members 340 and 350 toward each other until the engagement pin 347 and barb member 348 have pierced the mesh 180 and are engaged and locked into the engagement cavity 358. FIG. 12 shows the trimmed mesh 180 after four stay suture devices 310 have been applied by applicator 400. The four clips 330 have been applied along north-south and east-west axes. FIGS. 13 and 15 show a conventional configuration of a planar hernia mesh implant 500 prior to trimming by the surgeon. An outline 505 of the desired trimmed shape is seen on the top surface 502 of the implant 500. FIGS. 14 and 16 show the trimmed implant 510 having periphery 512.

Figure 17:
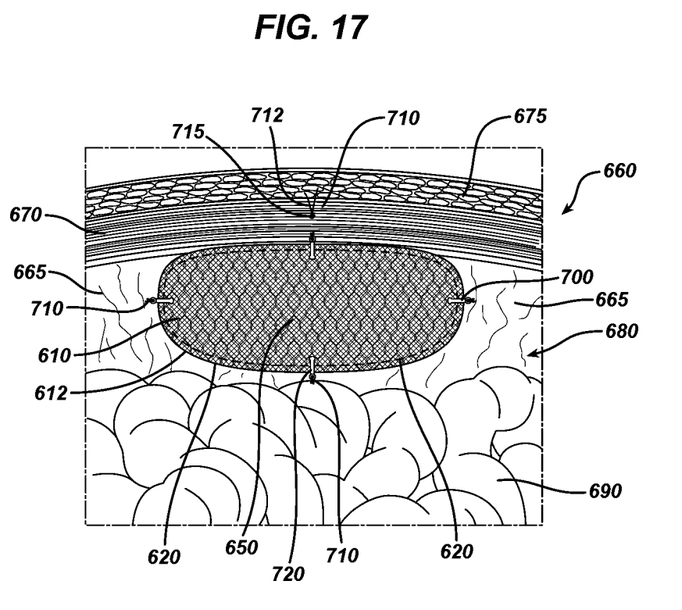
FIG. 17 is a partial perspective cross-sectional view of the abdomen of a patient showing the hernia mesh of FIG. 14 implanted in a patient and affixed to the patient's peritoneum and body wall adjacent to the patient's viscera and over a body wall defect; the stay suture devices can be seen mounted to the mesh with the stay sutures drawn up through the body wall tissue and knotted in place.
Figure 18:
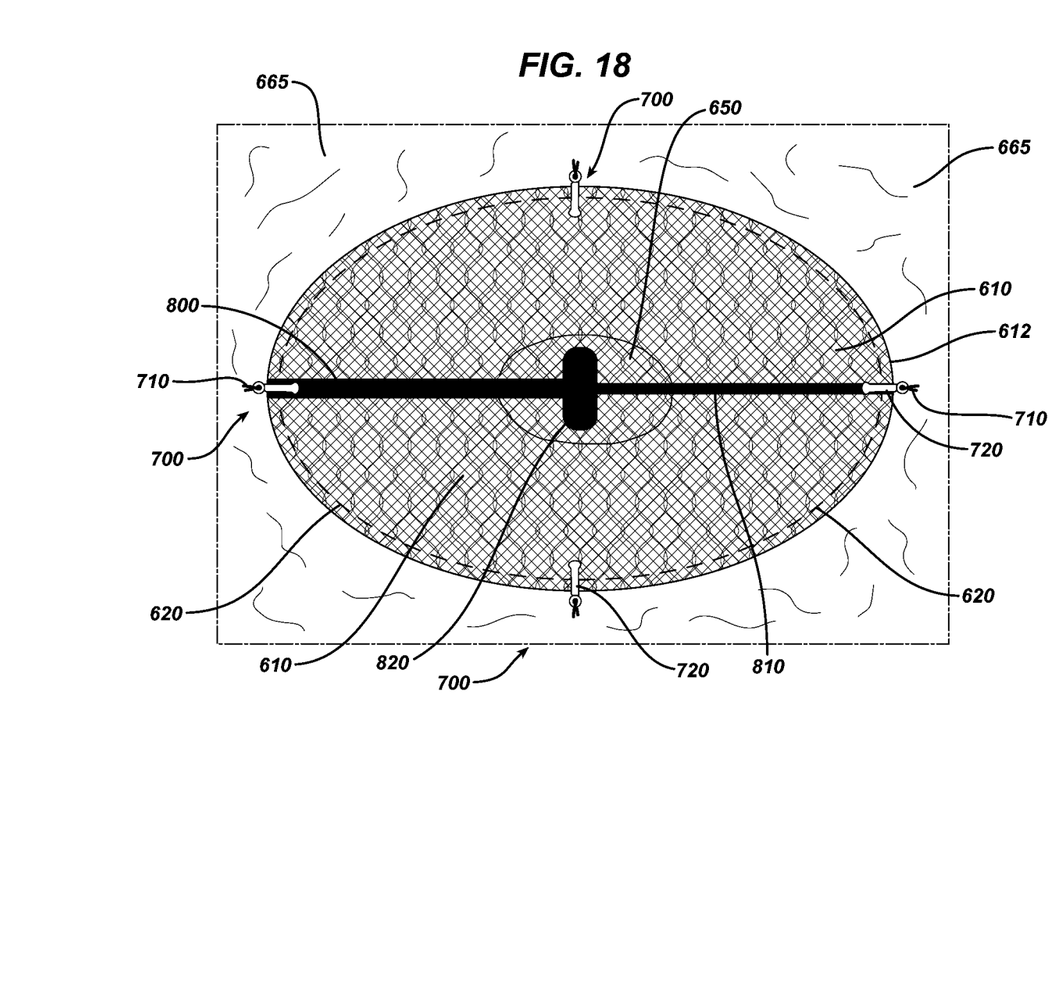
FIG. 18 is a plan view from the interior of the patient's abdominal cavity showing the hernia mesh implant in place on the inner surface of the patient's peritoneum over the hernia defect; the stay suture devices used to initially position and secure the implant are seen. The mesh is seen to have a positioning marker to assist the surgeon in properly positioning the mesh implant during the endoscopic procedure.

Referring now to FIGS. 17 and 18, a trimmed hernia mesh implant 610 is seen affixed to a patients' peritoneum 665. The mesh implant 610 is seen to have been trimmed by the surgeon prior to implantation by the surgeon. The implant 610 is seen to be maintained over the hernia defect 650 by conventional surgical tacks 620, such as Ethicon SecureStrap tacks available from Ethicon, Inc., Somerville, N.J. 08876 U.S.A. The hernia defect 650 extends into the body wall 660 surrounding the abdominal cavity 680. The patient's viscera 690 are seen in the body cavity 680 below the implant 610 and peritoneum 665. Stay suture devices 700 of the present invention are seen mounted to four locations about the periphery 612 of mesh implant 600. The stay suture devices 700 are seen to have sutures 710 and clips 720. Clips 720 are attached to the mesh periphery 612. The ends 712 of sutures 710 are seen to have been passed through the peritoneum 665 and into body wall 660, and ends 712 are knotted to form knots 715 in the fascial layer 670 below fat layer 675. The mesh implant 610 is seen to have an optional marker 800 indicating the intersecting longitudinal and latitudinal axes 810 and 820, respectively. The marker 800 aids the surgeon in properly positioning the implant 610 over the hernia defect 650.

The hernia mesh implants that may be used in the combinations and methods of the present invention include conventional flat mesh implants such as PHYSIOMESH Flexible Composite Mesh and ULTRAPRO Mesh from Ethicon, Inc., and other conventional, commercially available flat meshes, The following example is illustrative of the principles and practice of the present invention, although not limited thereto.

EXAMPLE

A patient is prepared for hernia repair surgery in a conventional manner. The patient presents with a ventral hernia. The surgeon uses a closed or endoscopic procedure to effect the repair. After insufflating the patient' abdominal cavity in a conventional manner, the surgeon places four conventional trocar cannulas into the abdominal cavity using conventional trocars. One cannula is used as a portal for a conventional endoscope, which is part of a conventional camera and remote display system. The remaining cannulas are used by the surgeon and assistants to access the surgical site. The site of the body wall defect and surrounding anatomy is remotely visualized by the surgeon and the operating team. The surgeon determines the size of the hernia defect and selects an appropriate size of a conventional hernia mesh implant, such as a PHYSIOMESH Flexible Composite Mesh implant available from Ethicon, Inc., Somerville, N.J. 08876 U.S.A.

The mesh implant is cut to size as required. The surgeon then inserts conventional endoscopic cutting and manipulating instruments through the cannulas into the patient's abdominal cavity to move any visceral extending through the body wall defect back into a proper position within the abdominal cavity. The hernia sack portion of the patient's peritoneum is then resected and approximated in a conventional manner. The surgeon affixes four stay suture devices of the present invention about the periphery of the trimmed hernia mesh at points north, south, east and west. The devices are attached by engaging the clips with an appropriate applicator instrument. The mesh implant with the attached stay suture devices is rolled or folded and inserted through a cannula into the patient's abdominal cavity. The surgeon then manipulates the repair patch into position using a conventional endoscopic grasper instrument. An incision is then made over one of the stay suture locations extending below the epidermis into the underlying body wall tissue. The surgeon then pushes the sharp distal end of a suture passer instrument through the remaining layers of the body wall below the incision and into the abdominal cavity. The ends of the stay suture are captured by the suture passer and withdrawn by the instrument from the body cavity. The free ends of the suture are then knotted with 5 to 10 surgical knots in the incision using conventional surgical knotting techniques. This procedure is repeated for each stay suture. With the hernia mesh implant secured in position by the stay sutures, the surgeon then utilizes a conventional hernia repair surgical tacker instrument, such as a SecureStrap instrument, to provide one or more concentric rows of tacks through the mesh implant and into the body wall of the patient. The mesh implant is now secured to the patient's body wall on the inner surface of the peritoneum over the hernia defect. This completes the hernia defect repair, and the trocar cannulas are withdrawn and the insufflated abdominal cavity is allowed to deflate. All incisions are then approximated in a conventional manner and the patient is moved to a recovery room.

Although this invention has been shown and described with respect to detailed embodiments thereof, it will be understood by those skilled in the art that various changes in form and detail thereof may be made without departing from the spirit and scope of the claimed invention.

We claim:

1. A stay suture device, comprising:
   a clip having first and second opposed leg members connected by a hinge member, the leg members having proximal ends and distal ends, and opposed inner faces, the leg members having a first open configuration and a second closed configuration;
   a suture eyelet member extending proximally from the hinge member, the eyelet member having an open passageway for receiving a section of a surgical suture;
   a locking mechanism associated with the distal ends of the leg members to lock the leg members in the second closed configuration; and,
   a surgical suture slidably mounted to the eyelet member, wherein the suture has two free ends.

2. The device of claim 1, wherein the locking mechanism comprises a locking member extending downwardly from the inner surface of the distal end of the first leg member, and a locking cavity on the distal end of the second leg member for receiving and retaining a section of the locking member.

3. The device of claim 1, wherein the clip comprises a biocompatible material selected from the group consisting of absorbable polymers, metals, ceramics, and non-absorable polymers.

4. The device of claim 1, wherein the suture comprises a material selected from the group consisting of absorbable polymers and non-absorbable polymers.

5. The device of claim 1, wherein the suture is a monofilament suture.

6. The device of claim 1 wherein the suture is a multifilament suture.

7. The device of claim 1, wherein the locking mechanism comprises a downwardly extending pin member having a distal piercing barb extending from the inner surface of a distal end of one leg member and a cavity extending into the inner surface of the inner surface on the distal end of the other leg member, such that the pin member and barb are matingly engaged by the cavity.

8. The device of claim 7, wherein the cavity extends through the leg member.

9. The device of claim 7, wherein the cavity is surrounded by a plurality of engagement members radially extending into the cavity.

10. The combination, comprising;
A. a hernia mesh implant having a periphery; and,
B. a stay suture device, comprising:
a clip having a first and second opposed leg members connected by a hinge member, the leg members having proximal ends and distal ends, and opposed inner faces, the leg members having a first open configuration and a second closed configuration;
a suture eyelet member extending proximally from the hinge member, the eyelet member having an open passageway for receiving a section of a surgical suture;
a locking mechanism associated with the distal ends of the leg members to lock the leg members in the second closed configuration; and,
a suture slidably mounted to the eyelet member, wherein the suture has two free ends,
wherein the clip is mounted to the periphery of the mesh implant such that the mounted clip is in the second closed configuration.

11. The combination of claim 10, wherein the locking mechanism comprises a locking member extending downwardly from the inner surface of the distal end of the first leg member, and a locking cavity on the distal end of the second leg member for receiving and retaining a section of the locking member.

12. The combination of claim 10, wherein the clip comprises a biocompatible material selected from the group consisting of absorbable polymers, metals, and non-absorbable polymers.

13. The combination of claim 10, wherein the suture comprises a material selected from the group consisting of absorbable polymers and non-absorbable polymers.

14. The combination of claim 10, wherein the suture is a monofilament suture.

15. The combination of claim 10 wherein the suture is a multifilament suture.

16. The combination of claim 10, wherein the locking mechanism comprises a downwardly extending pin member having a distal piercing barb extending from the inner surface of a distal end of one leg member and a cavity extending into the inner surface of the inner surface on the distal end of the other leg member, such that the pin member and barb are matingly engaged by the cavity.

17. The combination of claim 16, wherein the cavity extends through the other leg member.

18. The combination of claim 16, wherein the cavity is surrounded by a plurality of engagement members radially extending into the cavity.

19. A method of affixing stay sutures to a hernia mesh implant, comprising the steps of;
providing a stay suture device, the device comprising:
a clip having a first and second opposed leg members connected by a hinge member, the leg members having proximal ends and distal end, and opposed inner faces, the leg members having a first open configuration and a second closed configuration;
a locking mechanism associated with the distal ends of the leg members to lock the members in the second closed configuration;
a suture eyelet member extending proximally from the hinge member, the eyelet member having an open passageway for receiving a section of a surgical suture; and,
a suture slidably mounted to the eyelet member, the suture having two free ends;
mounting the clip to a periphery of a hernia mesh implant such that the clip is in the second closed configuration; and,
capturing the free ends of the suture with a suture passing instrument.

20. A method of repairing a body wall defect with a mesh implant, comprising the steps of;
providing a stay suture device, the device comprising:
a clip having a first and second opposed leg members connected by a hinge member, the leg members having proximal ends and distal ends, and opposed inner faces, the leg members having a first open configuration and a second closed configuration;
a locking mechanism associated with the distal ends of the leg members to lock the leg members in the second closed configuration;
a suture eyelet member extending proximally from the hinge section, the eyelet member having an open passageway for receiving a member of a surgical suture; and,
a suture slidably mounted to the eyelet member, the suture having two free ends;
mounting at least one clip to a periphery of a mesh implant such that the clip is in the second closed configuration and the leg members are locked;
positioning the mesh implant over a body wall defect and pulling the suture through at least a section of a body wall surrounding the body wall defect by capturing the free ends of the suture with a suture passer instrument;
knotting the free ends of the suture together in the body wall; and,
securing the mesh implant to the body wall over the defect with surgical tacks, thereby repairing the body wall defect.

* * * * *